(12) United States Patent
Shlezinger et al.

(10) Patent No.: US 8,098,368 B2
(45) Date of Patent: Jan. 17, 2012

(54) METHOD FOR EVALUATION OF A GEMSTONE

(75) Inventors: Haim Shlezinger, Rosh Pina (IL); Ran Ziskind, Rosh Pina (IL); Adam Devir, Haifa (IL); Dan Sheffer, Rakefet D.N. Misgav (IL)

(73) Assignee: Galatea Ltd., Rosh Pina (IL)

( * ) Notice: Subject to any disclaimer, the term of this patent is extended or adjusted under 35 U.S.C. 154(b) by 547 days.

(21) Appl. No.: 11/990,693

(22) PCT Filed: Aug. 21, 2006

(86) PCT No.: PCT/IB2006/052884
§ 371 (c)(1),
(2), (4) Date: Feb. 20, 2008

(87) PCT Pub. No.: WO2007/023444
PCT Pub. Date: Mar. 1, 2007

(65) Prior Publication Data
US 2009/0147241 A1 Jun. 11, 2009

(30) Foreign Application Priority Data
Aug. 22, 2005 (DE) .......... 10 2005 039 679

(51) Int. Cl.
*G01N 21/00* (2006.01)
(52) U.S. Cl. .......... 356/30; 356/31
(58) Field of Classification Search ........ 356/30–31
See application file for complete search history.

(56) References Cited

U.S. PATENT DOCUMENTS

| | | | |
|---|---|---|---|
| 2,494,078 A | 1/1950 | Woodruff | |
| 2,627,276 A | 2/1953 | Eggleton | |
| 2,869,417 A | 1/1959 | Allen | |
| 3,437,402 A | 4/1969 | Levins | |
| 3,867,032 A | 2/1975 | Bruck | |
| 4,049,350 A | 9/1977 | Bruck | |
| 4,112,955 A | 9/1978 | Gollel | |
| 4,152,069 A * | 5/1979 | Bruck | 356/30 |
| 4,259,011 A | 3/1981 | Crumm et al. | |
| 4,394,580 A | 7/1983 | Gielisse | |
| 4,521,073 A | 6/1985 | Murakami et al. | |
| 5,242,203 A | 9/1993 | Agnew et al. | |
| 5,253,103 A | 10/1993 | Boyd et al. | |
| 5,379,102 A | 1/1995 | Takeuchi | |

(Continued)

FOREIGN PATENT DOCUMENTS

BE 1013663 5/2002

(Continued)

OTHER PUBLICATIONS

Saker "The Optical Properties of Liquid Selenium", Proceedings of the Physical Society, Section B, 65: 785-787, 1952. Fig.3.

(Continued)

*Primary Examiner* — Tarifur Chowdhury
*Assistant Examiner* — Tara S Pajoohi
(74) *Attorney, Agent, or Firm* — Greenberg Traurig, LLP

(57) ABSTRACT

A method of determining the position of inclusions in a gemstone, comprising:
  (a) placing the gemstone within a material having a refractive index within 0.5, optionally 0.2 or 0.1, of that of the gemstone;
  (b) illuminating the gemstone and imaging the illuminated gemstone; and
  (c) determining the position of inclusions based on images of the inclusions in the images.

28 Claims, 3 Drawing Sheets

U.S. PATENT DOCUMENTS

| | | | |
|---|---|---|---|
| 5,515,157 | A | 5/1996 | Can |
| 5,905,584 | A | 5/1999 | Osugi |
| 5,966,673 | A | 10/1999 | Shannon, Sr. |
| 6,014,208 | A | 1/2000 | Welbourn et al. |
| 6,020,954 | A | 2/2000 | Aggarwal |
| 6,239,867 | B1 | 5/2001 | Aggarwal |
| 6,473,164 | B1 | 10/2002 | De Jong et al. |
| 6,813,007 | B2 | 11/2004 | Lapa et al. |
| 7,001,038 | B2 | 2/2006 | Bock et al. |
| 7,105,822 | B1 * | 9/2006 | Beesley ............... 250/341.1 |
| 7,324,188 | B1 | 1/2008 | Beesley |
| 7,755,072 | B2 * | 7/2010 | Porat ................. 250/559.22 |
| 2002/0030039 | A1 | 3/2002 | Kerner |
| 2002/0052170 | A1 | 5/2002 | Holloway |
| 2003/0107722 | A1 | 6/2003 | Klingler |
| 2003/0223054 | A1 | 12/2003 | Warwick |
| 2004/0051861 | A1 | 3/2004 | Bray |
| 2004/0141320 | A1 | 7/2004 | Bock et al. |
| 2005/0036132 | A1 | 2/2005 | Lapa et al. |
| 2005/0117145 | A1 * | 6/2005 | Altman et al. ............ 356/30 |

FOREIGN PATENT DOCUMENTS

| | | |
|---|---|---|
| EP | 1158293 | 11/2001 |
| EP | 1211503 | 6/2002 |
| EP | 131994 | 4/2004 |
| EP | 1630549 | 3/2006 |
| JP | 60-262036 | 12/1985 |
| RU | 2 035 039 C1 | 5/1995 |
| RU | 2 054 656 C1 | 2/1996 |
| WO | WO 89/05280 | 6/1989 |
| WO | WO 89/12816 | 12/1989 |
| WO | WO 94/00399 | 1/1994 |
| WO | WO 96/04409 | 2/1996 |
| WO | WO 97/04302 | 2/1997 |
| WO | WO 99/61890 | 12/1999 |
| WO | WO 02/31474 | 4/2002 |
| WO | WO 02/46725 | 6/2002 |
| WO | WO 83/00389 | 2/2003 |
| WO | WO 03/099054 | 12/2003 |
| WO | WO 03/103434 | 12/2003 |
| WO | WO 2005/052540 | 6/2005 |

OTHER PUBLICATIONS

Deetlefs et al. "Neoteric Optical Media for Refractive Index Determination of Gems and Minerals", New Journal of Chemistry [Online], 30: 317-326, 2006. p. 317, col. 1, Line 12—p. 318, col. 1, Line 2, p. 324, col. 2—p. 326, col. 1, Figs.1, 5-8.

Larsen Jr. et al. "Measurement of the Refractive Index", Interantional Tables for Crystallography, XP009101445, C(Chap.3.3): 144, 2004. § [3.3.2].

McCormick "Advanced and Refined Technique in the Petrographic Study of Crystalline Refractories", Journal of the American Ceramic Society, XP009101414, 19(1-2): 7-13, Jan. 1936. p. 7, col. 2—p. 9, col. 1, Line 5, Fig.1, Tables I, III.

West "Immersion Liquids of High Refractive Index", The American Mineralogist [Online], XP002484248, 21: 245-249, 1936. Retrieved From the Internet: URL:http://www.minsocam.org/ammin/AM21/AM21_245.pdf>.

Meyrowitz, R. "A Compilation and Classification of Immersion Media of High Index of Refraction"; U.S. Geological Survey, Washington 25, D.C.; pp. 398-409, (1954).

Meyrowitz, R., et al. "Immersion Liquids of High Refractive Index"; pp. 746-750, (1951).

Merwin, H.E. & Larsen, E.S. Jr. "Mixtures of amorphous sulphur and selenium as immersion media for the determination of high refractive indices with the microscope"; Am. J. Sci. 34. 42-47, (1912).

Tatarsky, V.B. "Crystal Optics and the Immersion Method of Mineral Assaying"; permitted by the USSR Ministry of Higher and Vocational Secondary Education; 1965; pp. 213-215; Nedra Publishing House, Moscow.

Anderson B., B.W. "Gem Testing"; 1988; Moscow "MIR"; Butterworths.

* cited by examiner

METHOD FOR EVALUATION OF A GEMSTONE

RELATED APPLICATIONS

This Application is a National Phase of PCT Patent Application No. PCT/IB2006/052884 having International Filing Date of Aug. 21, 2006, which claims the benefit of German Patent Application No. 10 2005 039 679.8 filed on Aug. 22, 2005. The contents of the above Applications are all incorporated herein by reference.

FIELD OF THE INVENTION

The present invention relates to the determination of the value of gemstones. In particular, but not limited to, it relates to location and properties of internal flaws and their effects on a rough stone and polished stone value.

BACKGROUND OF THE INVENTION

The terms 'gem', 'gemstone' and 'stone' are used synonymously with the usual meaning referring to minerals such as diamonds, sapphires, rubies, emeralds and so on. Still, in particular cases, without compromising generality, diamonds will be used The terms 'inclusion', 'flaw' and 'defect' are used synonymously indicating an individual discernable visual irregularity inside the gem.

The term 'dividing plane' relates to planes through which a stone is sawed, cleaved or cut by any method into separate parts.

Gemstones, as an ornamental object rather than an industrial one, are valued by their appearance. In gemology, the quality of a gem such as a diamond, is typically determined by the "4C's", Clarity (internal perfection of the stone), Color (colorless being the more expensive), Cut (consisting of shape, proportions, symmetry, and polish), and Carat (weight).

As for clarity, it is important to identify the location and size of flaws inside a rough stone in order to determine the preferred dividing planes that would yield the greatest value from a given stone. Likewise it is important to identify flaws in a polished stone in order to determine its value.

Everyday practice is a visual examination of the stone by experts who try to assess the location and size of the flaws using their experience and following industry rules. Still, it is a human subjective judgment that depends on a particular person's skill and experience and may vary between different individuals and circumstances. Moreover, when a parcel of gemstones is to be evaluated, it could take a long time to assess each stone, so that the parcel value is deduced upon the examination of representative stones only.

To overcome the manual inconsistency and the labor involved, optical methods and devices have been proposed for the detection of flaws in stones. However, the high refractive index of gems, especially diamonds, causes large refractions of incoming and outgoing light and total internal reflections resulting in multiple deflected images of the flaws.

U.S. Pat. No. 4,259,011 describes how to identify the presence of inclusions but not their location. European patent 1,211,503, presents a possible solution for the locating of inclusions in a transparent and at least partially polished diamond by imaging the diamond twice and analyzing the images by computer so as to localize an inclusion with respect to the outer surface of the diamond. Although this patent makes reference to a refractive index correction factor to be included in the computer's calculations, it does not provide a solution to multiple images produced by a single inclusion.

U.S. Pat. No. 4,049,350 teaches eliminating the refractions and reflections at the facets of a cut stone by submerging the stone in a solution of similar refraction index. It describes how to locate an inclusion in a two dimensional plane by aiming a narrow laser beam at a preferred angle to a particular facet.

U.S. Pat. No. 4,152,069 also teaches submerging a cut stone in such a solution and how to find the inclusion within a three dimensional volume.

Both latter references do not disclose any information on the medium they used to closely match the refraction index of the gem, this being particularly problematic for diamonds that have a very high refraction index. As far as is known to the present inventors, no such liquid has been suggested in the art.

A paper entitled "The Optical Properties of Liquid Selenium" (E. W. Saker, Proc. Phys. Soc. 1952, pp. 785-787) provides some experimental results, including the refraction index of solid and molten selenium in the near infrared region with respect to temperature and wavelength.

The disclosures of all of the above cited references are incorporated herein by reference.

SUMMARY OF THE INVENTION

An aspect of some embodiments of the invention relates to a method and apparatus for evaluating a gemstone with respect to its potential for producing polished gems responsive to the position, size and the color (dark/bright) of flaws relative to the external surfaces in the rough stone.

An aspect of some embodiments of the invention relates to a method and apparatus for evaluating a gemstone in terms of cost and value of potential polished gems responsive to the position and size of flaws in the rough stone.

An aspect of some embodiments of the invention relates to a method and apparatus for evaluating a gemstone in terms of cost and value of polished gems responsive to the position and size of flaws in the stone.

An aspect of some embodiments of the invention relates to a method and apparatus for deciding on the sawing planes in a gemstone to increase its potential value responsive to the position and size of flaws in the rough stone.

An aspect of some embodiments of the invention relates to a method and apparatus for substantially reliable finding of the positions of inclusions within the structure of a gemstone which may be even a rough irregular or uncut stone, provided that it is not coated by different material.

In an embodiment of the invention, the position of the inclusion with respect to the outside geometry is determined. Optionally, this information is used to determine possible sawing planes and/or an optimal set of sawing planes for the stone (optimal with respect to resultant gems). The internal stresses in the stone are taken in consideration when the sawing plane is defined. Alternatively or additionally a value of the rough stone and/or cut and polished gemstones that can be derived from the rough stone is determined.

Exemplary embodiments of the latter method involve 3 actions: (a) determining the external structure of the stone, (b) locating the inclusions and determining their geometry, and (c) relating the positions of the inclusions to the external structure of the stone.

In an embodiment of the invention, an optical probe, comprising a light source and a sensor, is used to scan the stone and detect its external structure. The stone is moved relative to the probe in order to capture its structure from various points of views. The optical probe is, optionally, one of the following commercially available devices of the following techniques: Triangulation, Circumferential Triangulation, Structured light and Achromatic Confocal or Conoscopic Holography. The probe may be a spot probe (the probe measures one point at a time), a line probe (the probe illuminates a line on the object and measures along this line) or an area probe (the probe illuminates an area on the object and measure the whole area at a time).

Other methods of determining the external structure of the gemstone, as known in the art, can be used, for example a mechanical probe.

The coordinates and datum of the external inspection setup are marked for correlation with the internal examination.

Optionally and additionally, internal stresses in the stone are detected and recorded using tools of the art, such as a polarizing apparatus.

In an embodiment of the invention, the gem is immersed in a medium having a refraction index substantially comparable to that of the gem, at least for a particular wavelengths band of light and temperature. Thus the refractions and internal reflections and multiple deflected images of inclusions are substantially eliminated. Light entering the stone will largely pass through it, but an inclusion will disperse the light so that viewing the stone from a particular direction will produce an image with a dark region relative to a bright background, with the inclusion being on that line of sight (i.e. not substantially deflected).

Optionally and preferably, the medium has a low enough viscosity to allow the material to enclose the stone. Material with such low viscosity will enable looking into a "Frosty" stone (a stone with a rough external surface that looks milky to the naked eye).

As the refraction index of any material is affected by the wavelength and the temperature, these parameters should be controlled in order to achieve a close match between the refraction index of the stone and the medium; that is, the stone and the immersing medium should be kept in a suitable temperature and the light filtered to allow only the appropriate wavelengths to reach the detector.

As a non-limiting preference, the medium should be substantially non-toxic and safe for industrial use.

Optionally said medium comprises at least one chalcogenide element in group 16 of the periodic table, such as sulphur, selenium or tellurium.

Preferably for the index of refraction close to that of a diamond, the medium comprises selenium; preferably selenium comprises a significant part of the medium; optionally the selenium part is in a molten phase and the diamond is imaged with infrared light; optionally the gemstone is immersed in the molten medium which subsequently solidifies, encasing the gemstone in a solid phase. Alternatively, the material is provided as part of a gel.

Optionally the medium may contain other ingredients to improve desired characteristics.

In an embodiment of the invention, the stone is fixed on a rotatable base and immersed in said medium. The stone is in a known position and rotation with respect to the setup coordinates. A light source illuminates the stone, and a suitable detector records its image for various orientations. The recorded image will comprise a distinctive impression of any detectable inclusion in the stone. The gem is imaged at a multiplicity of orientations as required for a consequent reconstruction of the inclusions position in the setup coordinates from the recorded images.

If the match in optical properties between the gemstone and the surrounding medium is perfect, then the inclusions will be the only thing imaged (without deflection). If the match is not perfect there may be a "ghost" image of the external features, but refractions and internal reflections will be greatly reduced if not eliminated. In some situations it may be possible to eliminate separate determination of the external structure and determine that structure and the relationship between the position of the inclusion and the external structure from a single set of images.

In an embodiment of the invention the setup coordinates used in the gem reconstruction are matched with the coordinates of the setup used for the inclusion detection, optionally and preferably the same setup is used for both. Having a model of the external structure of the gem and the positions of inclusions in the matched or common setup coordinates, the inclusions' positions are mapped into the gem structure, alternatively or additionally, incorporated into the gem geometrical model.

In an embodiment of the invention the external geometry of the gemstone and the respective positions of the inclusions therein (both with respect to the setup coordinates) are combined to determine the position of the inclusions in the gemstone. Optionally the positions of the inclusions are used to calculate dividing, e.g., sawing, planes to produce preferred polished gems. Optionally, the value of the polished gemstones is used to compute a preferred sawing plane or set of sawing planes. Optionally a value of the gemstone is established based on the value of the polished stones.

Optionally the preferred goal is largest flawless polished gems, so that the planes go through inclusion or isolating them.

Optionally the preferred goal is the highest value flawless polished gems such as better cut or shape at the expense of size whereby the planes go through inclusion or isolating them.

Alternatively, the preferred goal. is highest value polished gems, some of which optionally including flaws, for example larger size or better cut on the expense of clarity;

Alternatively or additionally, the preferred goal is the better effectiveness of value to cost such as value less cost, or value per cost ratio.

Optionally, the algorithm may be tuned to use a combination of criteria for preferred value goals.

Optionally or additionally, the algorithm reports, for a stone, a set of preferred planes according to the specified goal or goals. Alternatively or additionally, it reports a list of sets of planes ranked according to the preferred goal or goals.

Alternatively or additionally, for a set of said sawing planes of a stone the algorithm reports selected ones of the value of potential value of resultant polished gems, the cost involved, a value of cost effectiveness such as the value after cost deduction, and/or any other suitable value to cost relation.

Optionally or additionally, said report comprises the maximum net and/or gross (before cost) stone value.

Optionally, the stone model and respective sawing planes are recorded, and optionally reported, such that they can be read and construed for later use.

Optionally, any of the output of the aforementioned exemplary embodiments, namely, the stone structure, inclusions positions therein and preferred sawing planes, may be input into sawing and polishing machinery, optionally automatically.

In an embodiment of the invention, marks are made on the external surface of the stone to enable alignment of the stone for sawing. In an embodiment of the invention, the marks are made while the stone is in the set-up. Optionally, the marks are made by a laser.

There is thus provided, in accordance with an embodiment of the invention, a method of determining the position of inclusions in a gemstone, comprising:

(a) placing the gemstone within a material having a refractive index within 0.5, optionally 0.2 or 0.1, of that of the gemstone;

(b) illuminating the gemstone and imaging the illuminated gemstone; and (c) determining the position of inclusions based on images of the inclusions in the images.

In an embodiment of the invention, the method includes:
repeating (a) and (b) for a plurality of orientations of the gemstone with respect to the illumination and an imager used to image the gemstone,
wherein determining comprises:
determining the position of inclusions in three dimensional space based on images of the inclusions in the images.

In an embodiment of the invention, the material comprises a chalcogenide element in group 16, preferably selenium.

In an embodiment of the invention, the material is a liquid and wherein placing comprises immersing the gemstone in the liquid, optionally a molten material.

Optionally, the material and the gemstone are at a temperature of between 221 and 400 degrees Celsius.

In an embodiment of the invention, the material comprises a solid and wherein placing comprises encasing the gemstone in the solid. Optionally, the material and the gemstone are at a temperature of between 100 and 220 degrees Celsius.

In an embodiment of the invention, the illumination is in the infra-red, optionally, having a wavelength between 1 and 1.8 microns.

In an embodiment of the invention, the gemstone is a diamond. Optionally, the gemstone is unpolished. Alternatively, the gemstone is polished.

In an embodiment of the invention, the method includes:
obtaining a geometrical representation of the external surface of a gemstone relative to a respective coordinate system, wherein imaging comprises obtaining a geometrical representation of the flaws in the gemstone relative to the same coordinate system.

Optionally, the images comprise perceptible projections of the exterior of the gemstone and distinctive images of a non-deflected inclusion within a gemstone projection, such that a geometrical representation of the external surface of the gemstone can be obtained from said perceptible projections.

Optionally, obtaining the geometrical representation of the external surface includes irradiating the gemstone and determining a distance based on reflections from the surface.

In an embodiment of the invention, the method includes evaluating the gemstone.

Optionally, evaluating the gemstone includes determining one or more dividing planes for dividing the gemstone, based on the positions of the inclusions.

Optionally, evaluating the gemstone is responsive to the value of at least one potential polished gem yieldable by the gemstone. Optionally, the values of the potential polished gems are responsive to the size and geometry of potential flawless polished gems. Optionally, the values of the potential polished gems is responsive to the size of the potential polished gems. Optionally, the value of the potential polished gems is responsive to the cost of producing these gems.

Optionally, the method includes providing a plurality of sets of dividing planes each resulting is different sets of potential polished stones.

BRIEF DESCRIPTION OF THE DRAWINGS

Non-limiting examples of embodiments of the present invention are described below with reference to figures attached hereto, which are listed following this paragraph. In the figures, identical structures, elements or parts that appear in more than one figure are generally labeled with a same symbol in all the figures in which they appear. Dimensions of components and features shown in the figures are chosen for convenience and clarity of presentation and are not necessarily shown to scale.

DETAILED DESCRIPTION OF EMBODIMENTS OF THE INVENTION

In the following discussion a possibly present inclusion (or flaw or defect) in singular applies as well to a plurality of inclusions.

Figure 1:
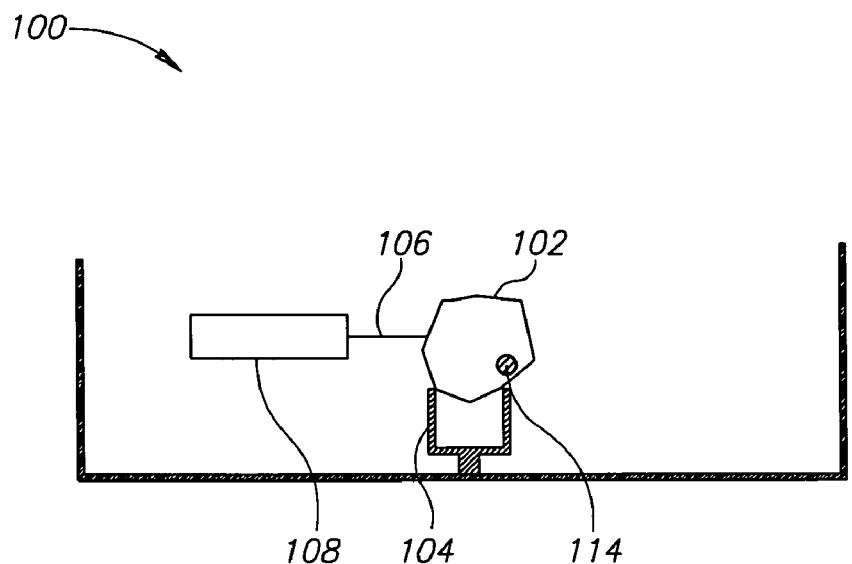
FIG. 1 is a schematic illustration of an imaging apparatus to determine the external structure of a gemstone, in accordance with an exemplary embodiment of the invention.

An apparatus 100 for the determination of the external structure of a gemstone, according to an exemplary embodiment of the invention, is schematically illustrated in FIG. 1.

A gemstone 102 (optionally with a floor 114) is fixed on a rotatable base 104 of a known position and orientation. An optical probe 108 with known position, measures the distance 106 to the stone by a method of the art as indicated in the summary. The stone is scanned and rotated, to provide a map of the external surface of the stone in the coordinates of the measuring system.

Figure 2:
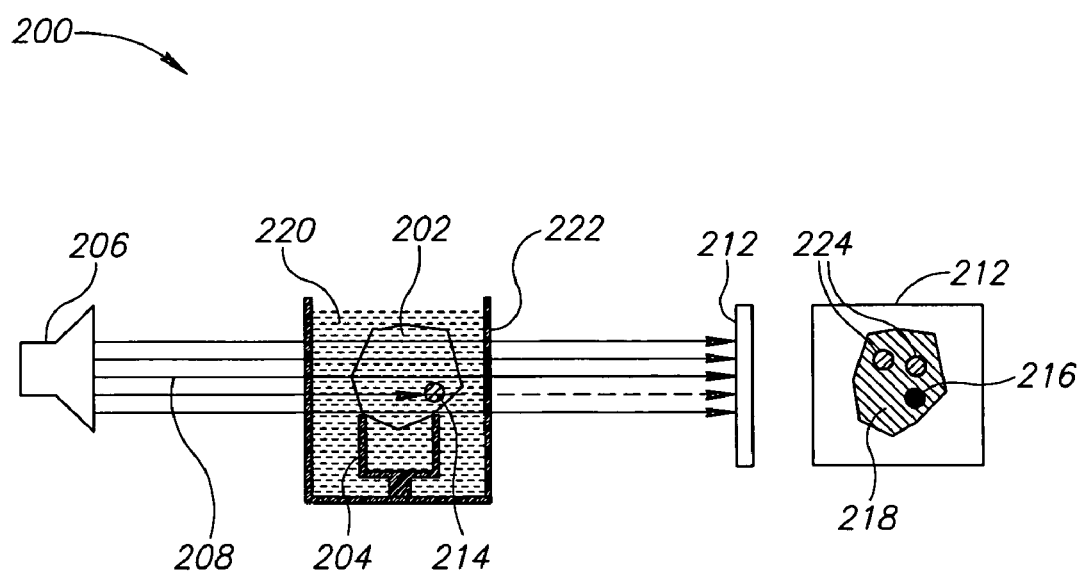
FIG. 2 is a schematic illustration of the use of an apparatus to determine the position of an inclusion in a gemstone, in accordance with an exemplary embodiment of the invention.

FIG. 2 schematically illustrates an apparatus 200 for the determination of the positions of inclusions within the stone.

A medium 220 with refractive index substantially comparable to that of the stone fills compartment 222 and covers the stone. The temperature of the medium and the wavelengths of the light are set so that the refraction index of the medium and the stone match as closely as practical. This immersion substantially eliminates the refractions and internal reflections in the stone and the multiple deflected images of inclusions. Light 208 entering the stone will largely pass through, but an inclusion 214 will disperse the light. The detector 212 is adapted to pass only the wavelength region substantially appropriate for the close refraction index. Thus, detector 212 detects and records the inclusion in its substantially true position 216 relative to a brighter background 218.

Figure 3:
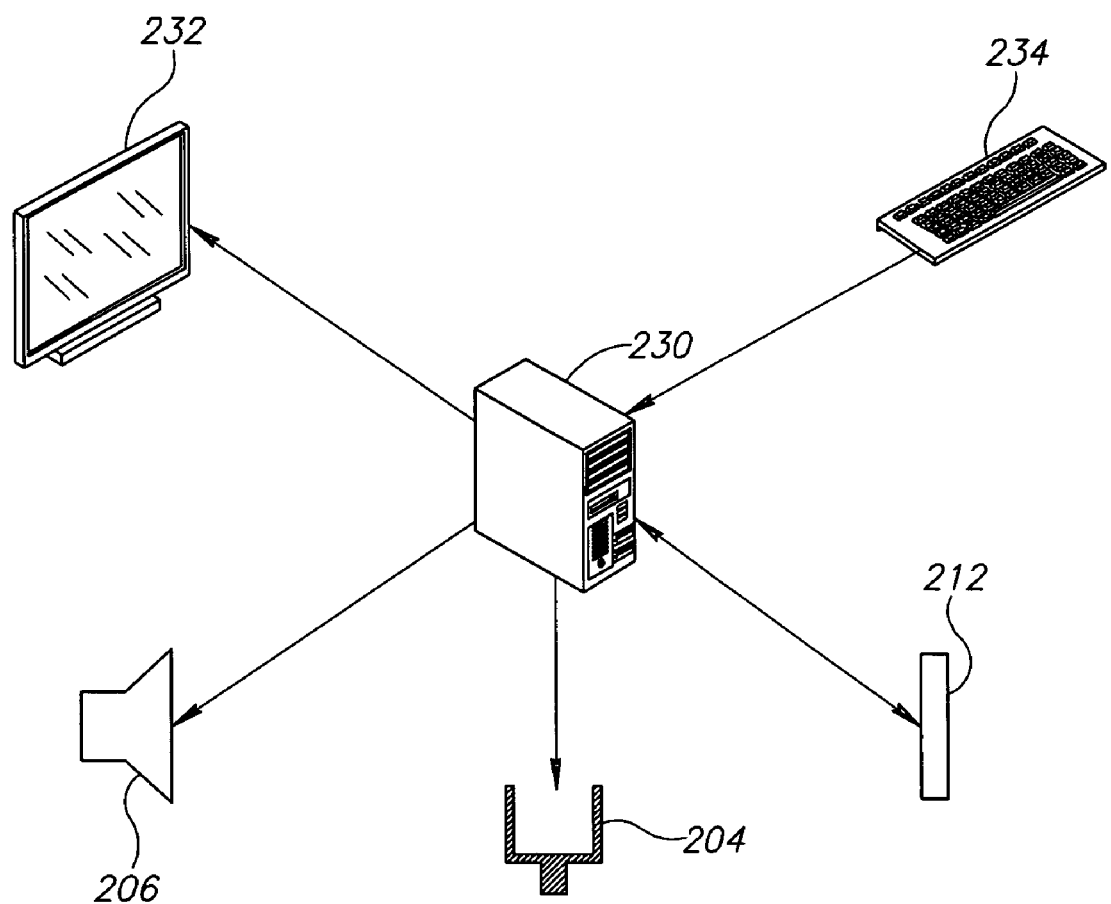
FIG. 3 is a schematic illustration of a controller and directions of primary signals with respect to the involved components of the apparatus of FIG. 2, in accordance with an exemplary embodiment of the invention.

Note that the brightness of the shadow 218 formed by the stone correlates with the difference of absorption of the light in the medium and in the stone. This shadow may be used to reconstruct the external surface of the stone Due to control sent from controller 230 (FIG. 3), base 204 is rotated and a plurality of images is detected and the controller receives and records them. These recorded projections are used to reconstruct the position of the inclusion with respect to the coordinates of apparatus 200. Known methods such as triangulation, back-projection, reverse Radon transform and others may be employed and optionally performed on controller 230, in order to construct the 3D geometry of the flaws from the series of 2D images. Optionally, controller 230 has an associated user interface including an input station 234, which may include a keyboard and/or mouse and/or a display 232 for displaying status and/or results of analysis of acquired data.

Since the coordinates of the outer contour are acquired in the same coordinate space as those of the inclusions the position of the inclusions can be mapped into the coordinates of the stone. Optionally, one or more marks are made on the rough stone, by a laser or the like (not shown), while the gem is in the apparatus to allow for easier alignment of the stone during the sawing operation. Alternatively or additionally, the stone transferred to a sawing station while still mounted in base 204.

In some embodiments, the refraction index of the medium 220 may differ to a certain extent from that of the stone 202 for the irradiating light 208. Consequently the detector detects and records into controller 230 a noticeable projection of the stone 218 together with a distinct direct image 216 of the inclusion (as well as some faint deflected images 224). Rotating base 204 for a plurality of orientations due to signals from controller 230, the respective images of the stone projection with the inclusion are detected and controller 230 receives and records them. Subsequently, ignoring the faint inclusions 224, the recorded images are used to reconstruct a combined geometrical model of the stone with the inclusion, optionally simultaneously.

Optionally detector 212 comprises a radiation sensitive solid-state device, or a matrix of photocells, or alternatively or additionally, a photographic film or other imaging device.

Medium 220 is optionally liquid or gel-like. Optionally the medium comprises at least one chalcogenide element in group 16 of the periodic table, such as sulphur, selenium or tellurium.

Optionally for diamonds, the medium substantially comprises molten selenium. At a temperature of approximately 250 degrees Celsius, for infrared light of wavelength approximately of 1.5 micrometers the refraction index of selenium is substantially close to that of diamonds under the same conditions.

Optionally for diamonds, the stone may be immersed in molten selenium which subsequently solidifies, encasing the stone in a solid phase. Optionally, the selenium (or other material) is mixed with a material that forms a gel. This may enable working at lower temperatures and providing better matches. For example, at a temperature of around 130 degrees Celsius and a wavelength near 1.2 micrometers there is low loss in solid selenium and a good match between the refraction index of diamond and selenium.

It is understood that increasing the temperature of medium 220 and stone 202 has two important effects. On the one hand, the viscosity of the selenium decreases, making for a better mechanical match between the rough surface of the stone and the medium. On the other hand, the refraction index of the medium and the stone do not track with temperature. Thus, the temperature and wavelength should be chosen to reflect a balance between these factors, which may depend, for example, on whether the stone is rough or not. Under various conditions, in various preferred embodiments of the invention, the wavelength may vary from 1 micrometer to 2 micrometers, and the temperature from 100 to 400 degrees Celsius.

Figure 4:
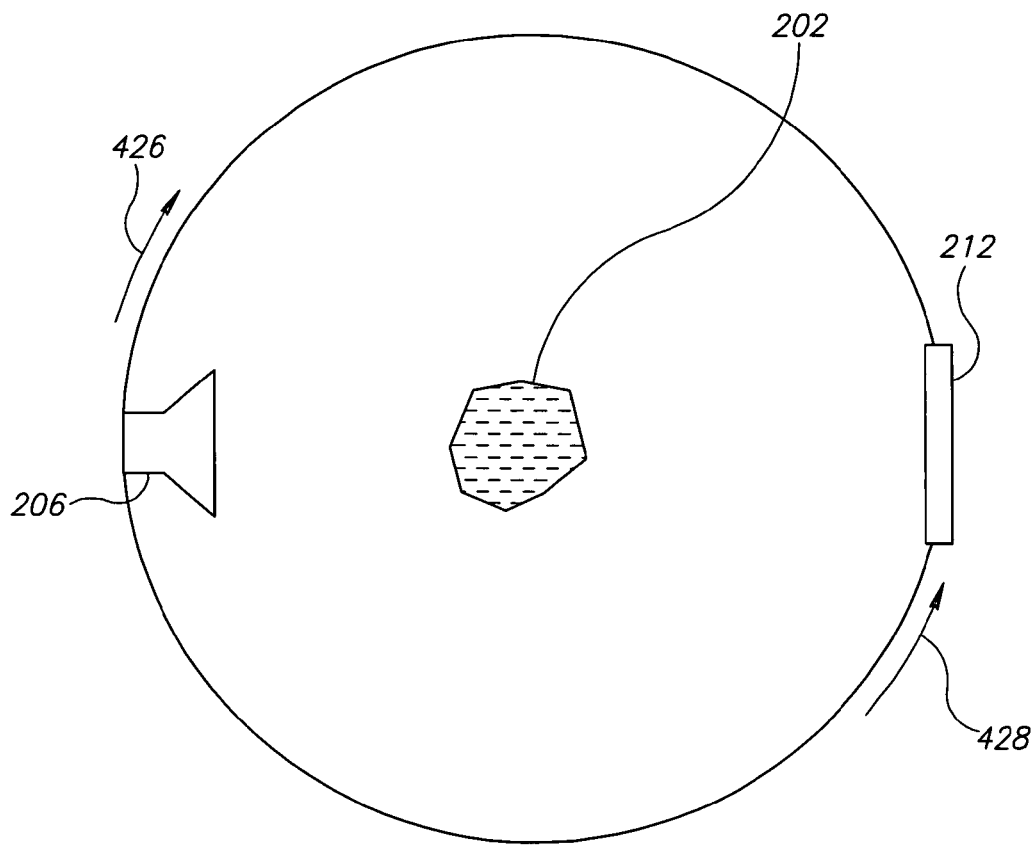
FIG. 4 is a schematic illustration of an alternative rotation of the imaging apparatus of FIG. 2, in accordance with an exemplary embodiment of the invention.

Note that values above are derived from the experimental results of "The Optical Properties of Liquid Selenium" cited in the background Optionally, instead of rotating base 204 with the gem, alternatively or additionally according to an exemplary embodiment, the base and gem may be stationary and the detector, optionally with the light source, will rotate around them due to signals from controller 230, as shown schematically in FIG. 4. Here gem 202 is stationary and source 206 and detector 212 are rotating in unison in either direction 426 or 428.

Figure 5:
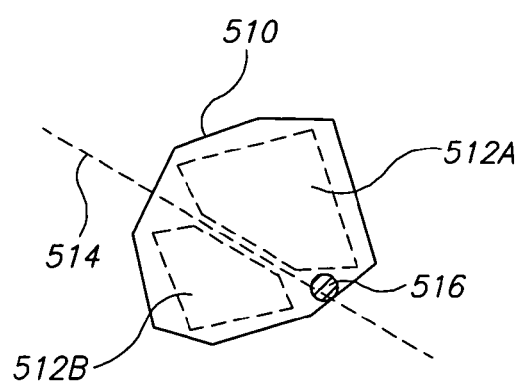
FIG. 5 is a schematic illustration of a rough stone with superimposed polished gems and an example of a dividing plane that eliminates an inclusion, in accordance with an exemplary embodiment of the invention.

Implemented in a program in controller 230, an exemplary embodiment of a method to determine the value of a gemstone with respect to its potential to produce polished gems responsive to the position and size of a flaw and to the internal stresses in the stone is described below, and partially depicted schematically in FIG. 5.

The program is provided with:
(a) A geometric model of the gemstone 510 and the inclusion 516 therein (for example, as disclosed above);
(b) Internal stresses in the stone. The internal stresses may be detected by tools of the art, such as a polarizer;
(c) The color of the stone. The color may be measured by tools of the art;
(d) Pre-defined scaleable geometrical models of polished gems (exemplified by 512a and 512b); and
(e) A value functions of the stone. The value is a function of the "4C" (Clarity, Cut, Color and Carat).

Each of the latter polished models is associated with a value on a common scale, optionally taking into account its size, color and clarity. Optionally and additionally, flaw size, shade and position inside the gem, affect a gem value; optionally or additionally, other factors may count for value. Optionally and additionally, polishing costs and other cost related factors may be associated with the model on the same scale.

The controller program fits models of cut gems into the model of the uncut stone. Various fitting techniques in the art may be used such as linear or non-linear optimization, heuristic algorithms, genetic algorithms and others.

The controller program defines sawing planes (514) and a value of the cut stones dependent on its characteristics and whether the stone includes inclusions or not. The value of the cut stone will depend on the size, position and type of the inclusion. The controller can be programmed to either present various options to the user or to automatically define a best use of the stone, based on predetermined criteria. Generally these criteria are based on the highest overall value of the gemstones that can be cut from the rough stone.

Optionally the preferred goal is the largest flawless polished gems whereby the planes pass through an inclusion or isolating it.

Optionally the preferred goal is the highest value flawless polished gems such as better cut or shape at the expense of size whereby the planes go through an inclusion or isolating it.

Optionally the preferred goal is the highest value polished gems, some of which optionally including flaws, for example larger size or better cut at the expense of clarity.

Alternatively or additionally, the preferred goal is the best effectiveness of value to cost such as value less cost, in combination with any of the preferred values as disclosed above.

Optionally, the decision may be tuned to use a combination of criteria for preferred value goals.

Optionally or additionally, the controller reports a set of preferred planes according to the specified goal or goals. Alternatively or additionally, it reports a list of sets of planes ranked according to the preferred goal or goals.

Alternatively or additionally, for a set of such dividing planes the controller reports the value of potential resultant polished gems; optionally and additionally, it reports the cost involved in producing them; optionally and additionally, it reports a value of cost effectiveness such as the value after cost deduction.

Optionally or additionally, the report comprises the stone value, represented as the value of the potential polished gems, optionally or additionally with some cost compensation.

Optionally, the stone model and respective dividing planes are recorded, and optionally reported such that they can be read and construed for practical use.

Optionally, any of the output of the aforementioned exemplary embodiments, namely, the stone structure, inclusions positions therein or preferred cutting planes, may be input into a machinery; optionally it is a sawing equipment; alternatively or additionally, a polishing equipment; optionally the input is automatic.

It should be understood that while the invention is described above in the context of uncut diamonds, it is equally applicable to cut and polished diamonds.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A method of determining a position of at least one inclusion in a diamond, comprising:
   (a) providing a material comprising a chalcogenide element in group 16;
   (b) increasing a temperature of the material to between 100 and 400 degrees Celsius to reach a molten state;
   (c) placing the diamond within the material;
   (d) adjusting an illumination with which the diamond is illuminated to a wavelength allowing the material to achieve a refractive index within 0.1 of that of the diamond when the material and the diamond are at the same temperature;
   (e) illuminating the diamond within the material by the illumination and imaging the illuminated diamond to obtain diamond images; and
   (f) determining the position of the at least one inclusion based at least in part on images of the at least one inclusion in the diamond images.

2. The method according to claim 1, further comprising: repeating (a) to (e) for a plurality of orientations of the diamond with respect to the illumination and an imager used to image the diamond,
   wherein the determining comprises
       determining the position of the at least one inclusion in three dimensional space based on images of the inclusions in the diamond images.

3. The method according to claim 1, wherein the material comprises selenium.

4. The method according to claim 3, wherein at least a portion of the material comprises elemental selenium.

5. The method according to claim 1, wherein the material is in the form of a gel.

6. The method according to claim 1, wherein the material is a liquid and wherein the placing comprises immersing the diamond in the liquid.

7. The method according to claim 1, wherein the refractive index of the material is within 0.1 of that of the diamond when the material and the diamond are at the temperature of between 221 and 400 degrees Celsius.

8. The method according to claim 1, wherein following the placing the diamond in the material, the material is allowed to solidify to result in the diamond being encased in the solid.

9. The method according to claim 8, wherein the refractive index of the material is within 0.1 of that of the diamond when the material and the diamond are at the temperature of between 100 and 220 degrees Celsius.

10. The method according to claim 1, wherein said refractive index of the material is within 0.1 of that of the diamond when the wavelength of the illumination is in the infrared.

11. The method according to claim 10, wherein the wavelength of the illumination has a wavelength between 1 and 1.8 microns.

12. The method according to claim 1, wherein the diamond is unpolished.

13. The method according to claim 1, wherein the diamond is polished.

14. The method according to claim 1, further comprising:
   (i) obtaining a geometrical representation of an external surface of the diamond relative to a respective coordinate system, and
   (ii) obtaining during the imaging of the diamond, a geometrical representation of the at least one inclusion in the diamond relative to the same coordinate system.

15. The method according to claim 14, and wherein the diamond images comprise perceptible projections of the external surface of the diamond and distinctive images of a non-deflected inclusion within a diamond projection, such that the geometrical representation of the external surface of the diamond can be obtained from the perceptible projections.

16. The method according to claim 14, wherein obtaining the geometrical representation of the external surface includes irradiating the diamond and determining a distance based on reflections from the external surface.

17. The method according to claim 14, further comprising evaluating the diamond.

18. The method according to claim 17, wherein the evaluating of the diamond includes determining one or more dividing planes for dividing the diamond, based at least in part on the position of the at least one inclusion.

19. The method according to claim 17, wherein the evaluating of the diamond is based at least in part on a value of at least one potential polished gem that can be produced from the diamond.

20. The method according to claim 19, wherein the value of the at least one potential polished gem is based at least in part on a size of the at least one potential polished gem.

21. The method according to claim 19, wherein the evaluating of the diamond including providing a plurality of sets of dividing planes, wherein each set of dividing planes produces a different set of potential polished gems.

22. The method according to claim 14, wherein step (i) is performed in the absence of the material and step (ii) is performed when the diamond is immersed in the material.

23. The method according to claim 19, wherein the value of the at least one potential polished gem is based at least in part on a size and geometry of at least one potential flawless polished gem.

24. The method according to claim 1, further comprising an external inspection of the diamond in the absence of the material for determining an external structure of the diamond; and relating to the external structure of the diamond the position of the at least one inclusion determined in step (f) based at least in part on the images of the at least one inclusion in the diamond images when the diamond is immersed in the material.

25. The method according to claim 24, wherein steps (a) to (f) constitute an internal examination of the diamond and are performed subsequent to, and in correlation with coordinates and datum of the external inspection.

26. The method according to claim 25, wherein the diamond in steps (a) to (f) is fixed on a rotatable base within the material in a known position with respect to the coordinates of the external inspection.

27. A method of determining a position of at least one inclusions in a diamond, comprising:
(a) scanning the diamond in a measuring system in the absence of an immersion material and providing a model of an external structure of the diamond;
(b) placing the diamond on a rotatable base within the immersion material, wherein the immersion material comprises a chalcogenide element in group 16;
(c) increasing a temperature of the immersion material to between 100 and 400 degrees Celsius to reach a molten state;
(d) adjusting an illumination with which the diamond is illuminated to a wavelength allowing the immersion material to achieve a refractive index within 0.1 of that of the diamond when the immersion material and the diamond are at the same temperature;
(e) illuminating the diamond within the immersion material by the illumination, and imaging the illuminated diamond within the immersion material to obtain diamond images;
(f) determining the position of the at least one inclusion based at least in part on images of the at least one inclusion in the diamond images; and
(g) mapping the position of the at least one inclusion into a diamond structure.

28. The method according to claim 27, wherein the immersion material has the refractive index when is heated to a predetermined temperature, the immersion material and the diamond are at the predetermined temperature when step (e) is performed.

* * * * *